United States Patent [19]

Hamas

[11] Patent Number: 5,496,370
[45] Date of Patent: Mar. 5, 1996

[54] GEL-LIKE PROSTHETIC DEVICE

[75] Inventor: Robert S. Hamas, Woodhill Medical Park, 8345 Walnut Hill La., Suite 120, Dallas, Tex. 75231

[73] Assignee: Robert S. Hamas, Dallas, Tex.; Trustee of the RHS GS-Trust

[21] Appl. No.: 93,816

[22] Filed: Jul. 19, 1993

Related U.S. Application Data

[63] Continuation of Ser. No. 850,534, Mar. 13, 1992, abandoned.

[51] Int. Cl.[6] ............................... A61F 2/02; A61F 2/12
[52] U.S. Cl. ............................................ 623/11; 623/8
[58] Field of Search ........................... 623/7, 8, 11, 12, 623/66

[56] References Cited

U.S. PATENT DOCUMENTS

| | | | |
|---|---|---|---|
| 2,542,619 | 2/1951 | Bernhardt | 623/7 |
| 2,842,775 | 7/1958 | Pangman | 3/36 |
| 3,189,921 | 6/1965 | Pangman | 3/36 |
| 3,366,975 | 2/1968 | Pangman | 3/36 |
| 3,559,214 | 2/1971 | Pangman | 3/36 |
| 3,663,968 | 5/1972 | Mohl et al. | 3/36 |
| 3,736,604 | 6/1973 | Carson, Jr. | 5/451 |
| 3,852,283 | 12/1974 | Köneke et al. | 3/36 |
| 3,852,832 | 12/1974 | McGhan et al. | 3/36 |
| 3,934,274 | 1/1976 | Hartley, Jr. | 3/36 |
| 4,205,401 | 6/1980 | Frisch | 3/36 |
| 4,264,990 | 5/1981 | Hamas | 3/36 |
| 4,430,764 | 2/1984 | Finkelstein | 5/450 |
| 4,507,810 | 4/1985 | Bartholdson | 6/8 |
| 4,715,076 | 12/1987 | Fogel et al. | 5/450 |
| 4,769,036 | 9/1988 | Moder | 623/8 |
| 4,955,907 | 9/1990 | Ledergerber | 623/8 |
| 4,969,899 | 11/1990 | Cox | 623/8 |
| 5,005,591 | 4/1991 | Austad | 623/8 |
| 5,104,409 | 4/1992 | Baker | 623/8 |
| 5,152,018 | 10/1992 | Lea | 5/450 |
| 5,171,269 | 12/1992 | Bark | 623/8 |
| 5,246,454 | 9/1993 | Peterson | 623/8 |
| 5,282,856 | 2/1994 | Ledergerber | 623/8 |

Primary Examiner—David Isabella
Attorney, Agent, or Firm—Webb Ziesenheim Bruening Logsdon Orkin & Hanson

[57] ABSTRACT

A prosthetic device, such as a mammary, testicular or chin prosthetic device, which includes a sealable envelope. The envelope is adapted to be filled with a fluid filler and is at least partially filled with a baffle forming material which acts as a baffle slowing the displacement of the fluid filler to achieve the desired tactile and aesthetic properties.

31 Claims, 1 Drawing Sheet

GEL-LIKE PROSTHETIC DEVICE

This is a continuation of application Ser. No. 07/850,534 filed on Mar. 13, 1992, now abandoned.

BACKGROUND OF THE INVENTION

1. Field of the Invention

This invention relates generally to artificial body members and, more specifically, to surgically implantable prosthetic devices.

2. Description of the Prior Art

It has become a practice in the field of surgery to place a prosthetic implant in various areas of the body under any one of various conditions. In cases where cancerous, precancerous, or other abnormal or damaged tissue has been removed, the prosthetic implant is often used as a replacement for the removed tissue and its purpose is to retain the original body contour. An implant of this character provides physical support for the surrounding body tissue, and by filling any voids that are created by the removal of the body tissue preserves the normal outward appearance and feel of the body. Prosthetic devices have also been used to enhance or augment the appearance of body parts.

Testicular prostheses have long been used for reconstruction following orchiectomy. The prostheses are available in numerous sizes and shapes and are implanted in the scrotum via a small incision.

Chin prostheses have long been used for augmentation of the chin to correct a deficiency. The prostheses are available in numerous sizes and shapes. Usually, chin prostheses are implanted via a small submental or intraoral incision into a pocket dissected in front of the mandible.

Breast prostheses have long been used for breast augmentation and for reconstruction such as following a mastectomy. The prostheses are available in numerous sizes and shapes including teardrop, round and low profile. Usually, breast prostheses are implanted via a small inframammary or pari-aerolar incision into a pocket dissected deep to the patient's own breast tissue in front of the pectoral muscle. In certain situations, the prosthesis may be placed behind the various chest muscles.

Some prosthetic devices have utilized an outer shell or envelope which is filled with a silicone gel. Some breast prosthetic devices have utilized an envelope which is filled with a combination of silicone gel and saline solution in separate compartments. These prior art devices have tactile properties similar to normal tissue, but suffer from certain disadvantages. First, some silicone may bleed the envelope and migrate into the tissue. Second, rupture of the envelope is difficult for a patient to detect. Third, silicone gel from a ruptured implant may cause an undesirable tissue response.

Some breast prosthetic devices have utilized an outer shell or envelope which is filled with a saline solution. The prior art saline solution filled prosthetic devices suffer from certain disadvantages and lack the proper appearance and tactile properties due to several factors. First, the saline solution displaces too quickly to give the proper tactile properties. Second, the ease of displacement of the saline solution can create a "fluid wave" in the implant presenting an unnatural look of the prosthetic device. Third, the quick displacement of the saline solution and air present in the implant can create an audible sound or "slosh". Fourth, the saline solution runs out of a superior portion of the implant to the inferior portion when the patient stands erect resulting in a lack of support of the overlying tissue in the superior area. Fifth, when the saline solution displaces from one area of the implant, the lack of volume in that area may result in visible wrinkling of the envelope.

The object of the present invention is to overcome some of the drawbacks of the prior art implants. The object of the present invention is to construct a surgically implantable prosthetic device which may be filled with saline and/or other fluids and which has the appropriate tactile appearance and other characteristics. The objects of the present invention are particularly related to breast, testicular and chin prosthetic devices, but are not limited thereto.

SUMMARY OF THE INVENTION

The objects of the present invention have been achieved by providing a surgically implantable prosthetic device which includes a sealable envelope defining an envelope interior and which is adapted to be filled with a fluid filler wherein the envelope interior includes a baffle forming material filling at least a portion of the envelope interior. The baffle forming material inside the envelope acts as a baffle to decrease the displacement rate of the fluid filler. This restriction of the ability of the fluid filler to move inside the envelope improves the desired tactile characteristics of the implant and reduces the "fluid wave" and "sloshing" effect of the implant. The baffle forming material may add support to the implant envelope minimizing wrinkles in the envelope. The baffle forming material may have a certain amount of elasticity to help give the implant the appropriate appearance and tactile characteristics.

A saline solution would be an appropriate choice for use as a fluid filler. Saline refers to any electrolyte combination together with water, however, the invention is not limited solely to the use of saline. Other fluids may be utilized such as, for example, peanut oil, organic polymers or protein fluids; furthermore, certain gases may possibly be utilized as effective fluid fillers. Peanut oil, in addition to greater viscosity, is more radio-translucent than saline solution. Therefore, a peanut oil filled implant will provide less interference with a mammography.

The prosthetic device utilizing saline or the like provides a safe and harmless prosthetic implant. If the outer shell is ruptured or compromised in any fashion, the saline is safely absorbed into the body tissue. Furthermore, the patient would observe the decrease in volume of the implant and quickly come in for a replacement. This quick indication of implant failure decreases the chance that there would be time for tissue to grow into the implant material after implant rupture due to lack of discovery.

The present invention may further enhance the safety of the device by placing the baffle forming material within one or more protective inner envelopes, which may or may not allow the fluid to flow through them but will contain any potential fragments of the baffle forming material in case the outer envelope ruptures. The baffle forming material may or may not be attached to the inner or outer envelopes.

It has been found that nylon mesh forms an acceptable baffle forming material. The mesh may be made from other material such as, for example, polypropylene or silicone elastomers. However, other baffle forming materials may be utilized such as, for example, gauze, sheets, nets, threads, tubes or sponges. The baffle forming material should have the appropriate baffle effect and may have some elastic properties as well. One or more of these baffle forming materials may be utilized in any combination and may be coated with other materials such as silicone elastomer or Teflon.

In a first embodiment of the present invention, the baffle forming material is formed in a central portion of the interior of the envelope such that a thin space is provided between the baffle forming material and the envelope in which the space substantially surrounds the baffle forming material. The space surrounding the baffle forming material allows for the insertion of a thin fluid layer surrounding the baffle forming material. The existence of the baffle forming material will become much less apparent at the surface of the implant, providing for the proper tactile properties of the device.

A second embodiment provides for a space which is substantially surrounded by the baffle forming material. This embodiment provides for a greater structural stability to the implant surface to minimize visible wrinkles in the implant.

A third embodiment provides for a plurality of locations for the baffle forming material which provides for structural support to the implant envelope while minimizing the adverse tactile effects of the baffle forming material.

A fourth embodiment provides for the baffle forming material to substantially fill the interior of the outer envelope.

The prosthetic device may be pre-filled prior to implantation or, alternatively, may be first implanted and then filled with the fluid filler. One or more valves may be provided on the outer and/or inner envelope for allowing for the filling of the inner and outer envelope interior with the fluid filler. It should be understood that the prosthetic device is particularly well adapted to be a mammary, testicular or chin prosthetic device but it is not limited thereto.

Other obvious advantages of the present invention will become apparent with the description of the preferred embodiments in association with the drawings.

DESCRIPTION OF THE PREFERRED EMBODIMENTS

Figure 1:
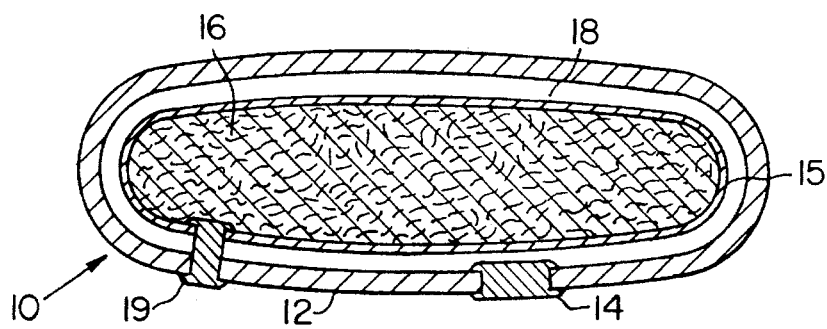
FIG. 1 is a cross-sectional side view of a first embodiment of the prosthetic device of the present invention.

FIG. 1 illustrates a surgically implantable prosthetic device 10 of the present invention which would be particularly adapted for use as a mammary prosthetic device. Prosthetic device 10 includes a sealable envelope 12. The sealable envelope 12 may be pre-formed as a fluid filled and completely sealed member or may be provided with a valve 14 as shown in FIG. 1. The valve 14 allows for filling of the interior of envelope 12 with a filling fluid after the manufacture of the device 10 either before or after implantation into the patient. Valve 14 would also allow for the controlled removal of filling fluid without damaging or destroying the device 10.

The sealable envelope 12 may be made out of any conventionally utilized material such as, for example, synthetic elastomers or nylon.

A baffle forming material 16 consists of one or more pieces and is positioned within the envelope 12 such that a space 18 is formed between envelope 12 and baffle forming material 16. This allows for a layer of fluid filler to be in space 18 resulting in the appropriate tactile properties for the device 10.

The envelope 12 is filled with a fluid filler, such as a saline solution. The term fluid filler refers to both gaseous and liquid fillers or any combination thereof. Baffle forming material 16 acts as a baffle slowing the displacement of the fluid filler. Nylon mesh has been found to operate effectively to form the baffle forming material 16, and meshes of polypropylene, Dacron or Teflon could also be utilized. Gauze, sheets, nets, threads, tubes, sponges or any combination thereof may be utilized as the baffle forming material 16 provided it acts as a sufficient baffle.

There is an optimum ratio of baffle forming material 16 to fluid filler for the device 10. The optimum ratio will depend on the specific type of prostheses, i.e. breast, testicular or chin, the baffle characteristics of the baffle forming material as well as the specific fluid filler used. For example, the optimum ratio of baffle forming material to fluid filler would be greater for a saline solution fluid filler than for an oil type of fluid filler.

Optionally, an inner envelope 15 may be provided around the baffle forming material 16. Inner envelope 15 may be a porous or nonporous member and is intended to maintain the baffle forming material 16 within the inner envelope 15 and, therefore, also within the outer envelope 12. If inner envelope 15 is nonporous, it may be pre-formed as a fluid filled and completely sealed member or may be provided with a valve 19 which allows for filling of the inner envelope 15 with a filling fluid after the manufacture of the device 10, either before or after implantation into the tissues. The inner envelope 15 will help prevent unwanted migration of portions or fragments of baffle forming material 16. A nylon net material would be sufficient to form the inner envelope 15.

Figure 2:
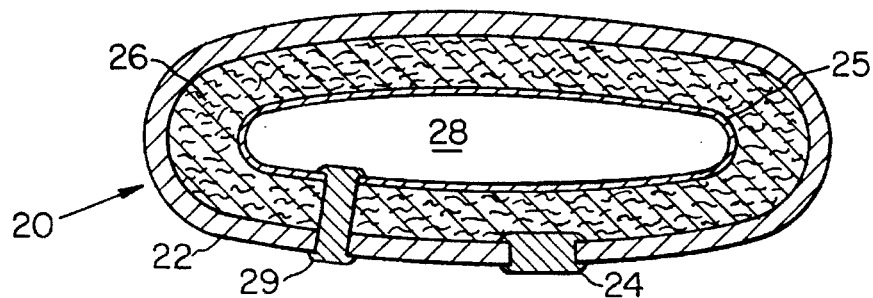
FIG. 2 is a cross-sectional side view of a second embodiment of the present invention.

The mammary prosthetic device 20 shown in FIG. 2 illustrates a slightly modified form of the present invention. The baffle forming material 26 is formed around the periphery of the interior of envelope 22 substantially surrounding a central space 28. The materials which may form the elements of device 20 are the same as described above in connection with FIG. 1. The difference lies in the placement of baffle forming material 26. The peripheral placement of baffle forming material 26 adds a degree of support to the envelope 22. The device 20 may also include a valve 24 within the envelope 22 and an inner envelope 25, with or without valve 29, substantially surrounding and encasing the baffle forming material 26.

Figure 3:
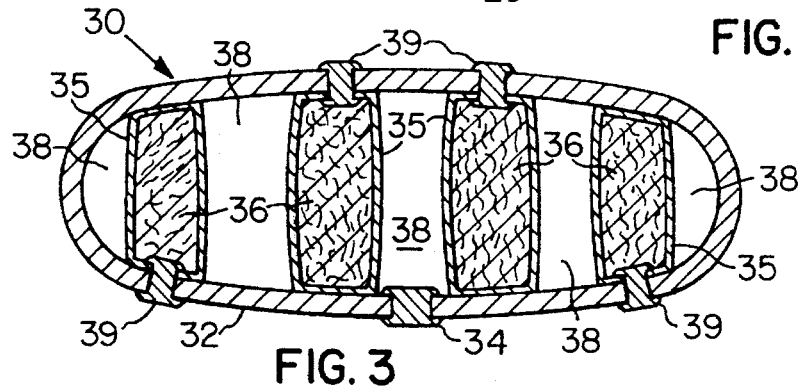
FIG. 3 is a cross-sectional side view of a third embodiment of the present invention.

The mammary prosthetic device 30 shown in FIG. 3 illustrates another form of the present invention. The baffle forming material 36 is placed within the envelope 32 at a plurality of locations, separated by space 38 which may or may not be interconnected. This arrangement allows for the baffle forming material 36 to add support to the envelope 22 while providing sufficient space 38 for the fluid filler to be adjacent the envelope 32 to provide proper tactile characteristics to the implant device 30. The implant device 30 may also include valve 34 in the envelope 32 and inner envelope 35, with or without valve 39, surrounding each section of baffle forming material 36.

Figure 4B:
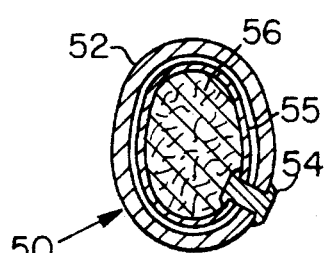
FIGS. 4A–4C are cross-sectional side views of a fourth embodiment of the present invention.
Figure 4A:
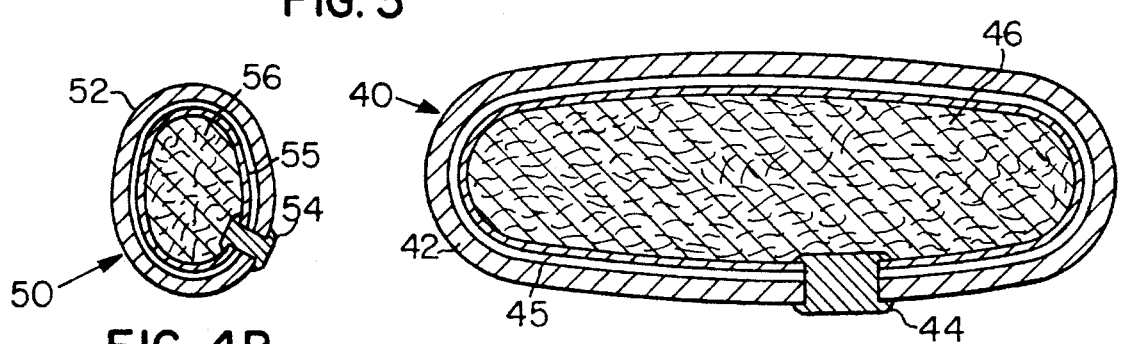
Figure 4C:
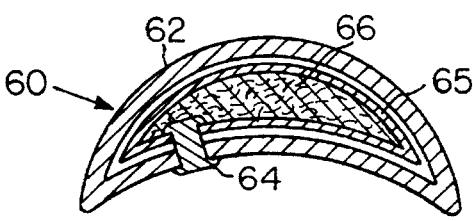

FIGS. 4A–4C illustrate a fourth embodiment of the present invention in which the baffle forming material substantially fills the interior of the envelope. The mammary prosthetic device 40, shown in FIG. 4A, provides baffle forming material 46 which substantially fills the interior of envelope 42. An optional valve 44 may be provided in envelope 42. An optional inner envelope 45, with or without a valve (not shown), may be provided surrounding the baffle forming material 46. The fluid filler will also fill the envelope 42 within the baffle forming material 46. A testicular prosthetic device 50, shown in FIG. 4B, is similar to the device 40; baffle forming material 56 substantially fills the interior of envelope 52. The prosthetic device 50 may also include a valve 54 and inner envelope 55 with or without a second valve (not shown). A chin prosthetic device 60, shown in FIG. 4C, also provides baffle forming material 66 substantially filling the envelope 62. The device 60 may optionally include valve 64 and inner envelope 65 with or without a separate valve (not shown).

A separate valve (19, 29, 39) will be required when a nonporous inner envelope (15, 25, 35, 45, 55, 65) is utilized to fill the interior of the inner envelope with an appropriate amount of fluid filler. These separate valves are shown extending through the outer envelope (22, 32, 42, 52, 62), however it is possible to place these valves only in the inner envelope and allow them to be filled through the valve (14, 24, 34, 44, 54, 64) provided in the outer envelope. Additionally, in regard to the embodiments shown with multiple valves, if a porous inner envelope or no inner envelope were included, any valve could be utilized alone to fill the entire implant with a suitable fluid filler.

It should be apparent to those skilled in the art that various modifications may be made to the present invention without departing from the spirit or scope of the present invention. The embodiments disclosed were for illustrative purposes only and are not intended to limit the scope of the invention. The scope of the present invention is defined by the following claims.

I claim:

1. A surgically implantable prosthetic device comprising:
   a sealable outer envelope defining an envelope interior and adapted to be filled with a fluid filler to maintain said fluid filler within said sealable outer envelope;
   an inner envelope positioned within said envelope interior of said sealable outer envelope and adapted to be filled with said fluid filler; and
   a baffle means for decreasing the displacement rate of said fluid filler positioned within said envelope interior of said outer envelope between said outer and inner envelopes and attached to at least one of said envelopes, said baffle means filling at least a portion of said envelope interior, wherein said baffle means allows for movement of said fluid filler through said baffle means in any direction.

2. The prosthetic device of claim 1, wherein said fluid filler is an electrolyte solution.

3. The prosthetic device of claim 1, wherein said fluid filler is a saline solution.

4. The prosthetic device of claim 1, wherein said fluid filler is organic.

5. The prosthetic device of claim 1, wherein said device is a mammary prosthetic device wherein at least a portion of said sealable envelope is curved.

6. The prosthetic device of claim 1, wherein said device is a testicular prosthetic device wherein at least a portion of said sealable envelope is curved.

7. The prosthetic device of claim 1, wherein said device is a chin prosthetic device wherein said sealable envelope has a substantially crescent shape in cross section.

8. The prosthetic device of claim 1, wherein said envelope includes a valve for allowing for the filling of said envelope interior with said fluid filler.

9. The prosthetic device of claim 1, wherein said baffle means includes mesh.

10. The prosthetic device of claim 1, wherein said baffle means includes sheets.

11. The prosthetic device of claim 1, wherein said baffle means is selected from the group consisting of sponges, threads, nets, gauze, tubes and combinations thereof.

12. The prosthetic device of claim 1, wherein said baffle means includes at least one silicone sheet.

13. The prosthetic device of claim 12, wherein said space is positioned between said baffle means and said envelope wherein said space substantially surrounds said baffle means.

14. The prosthetic device of claim 12, wherein a said baffle means is positioned at a plurality of locations within said envelope interior.

15. A surgically implantable prosthetic device comprising:
   a sealable outer envelope defining an envelope interior and adapted to be filled with a fluid filler to maintain said fluid filler within said sealable outer envelope;
   an inner envelope positioned within the interior of said sealable outer envelope and adapted to be filled with said fluid filler; and
   a baffle means for decreasing the displacement rate of said fluid filler positioned within the interior of said inner envelope and attached to said inner envelope, said baffle means filling at least a portion of said envelope interior, wherein said baffle means allows for movement of said fluid filler through said baffle means in any direction and said inner envelope encloses said baffle means.

16. The prosthetic device of claim 15, wherein said inner envelope is porous adapted to allow said fluid filler to flow therethrough.

17. The prosthetic device of claim 15, wherein said inner envelope in nonporous.

18. The prosthetic device of claim 17, wherein a valve is provided on said inner envelope.

19. The prosthetic device of claim 15, wherein a space is provided in said envelope interior which is not filled with said baffle means.

20. A surgically implantable prosthetic device comprising:
   a sealable outer envelope adapted to be filled with a fluid filler to maintain said fluid filler within said sealable outer envelope;
   an inner envelope positioned within said sealable outer envelope adapted to be filled with said fluid filler; and
   a mesh material positioned within said outer envelope between said outer and inner envelopes, wherein said mesh is attached to at least one of said envelopes.

21. A surgically implantable prosthetic device comprising:
   a sealable outer envelope defining an envelope interior adapted to be filled with a fluid filler to maintain said fluid filler within said outer sealable envelope;
   an inner envelope positioned within the interior of said sealable outer envelope and adapted to be filled with said fluid filler; and a mesh material positioned within said inner envelope, wherein said inner envelope encloses said mesh and said mesh is attached to said inner envelope.

22. The prosthetic device of claim 20, wherein said prosthetic device is a mammary prosthetic device wherein a portion of said sealable envelope is curved.

23. The prosthetic device of claim 20, wherein said prosthetic device is a testicular prosthetic device wherein a portion of said sealable envelope is curved.

24. The prosthetic device of claim 20, wherein said prosthetic device is a chin prosthetic device wherein said sealable envelope has substantially a crescent shape in cross section.

25. The prosthetic device of claim 20, wherein said mesh material is nylon.

26. The prosthetic device of claim 20, wherein said fluid filler is an electrolyte solution.

27. The prosthetic device of claim 26, wherein said electrolyte solution is a saline solution.

28. The prosthetic device of claim 20, wherein said mesh material is coated with silicone elastomer.

29. The prosthetic device of claim 20, wherein said mesh material is polypropylene.

30. The prosthetic device of claim 20, wherein said mesh material is Dacron.

31. The prosthetic device of claim 20, wherein said mesh material is Teflon.

* * * * *

UNITED STATES PATENT AND TRADEMARK OFFICE
CERTIFICATE OF CORRECTION

PATENT NO. : 5,496,370
DATED : March 5, 1996
INVENTOR(S) : Robert S. Hamas

It is certified that error appears in the above-indentified patent and that said Letters Patent is hereby corrected as shown below:

```
Title page, in section '[73] Assignee:', "RHS"
    should read --RSH--.
```

Signed and Sealed this

Eighteenth Day of June, 1996

Attest:

BRUCE LEHMAN

*Attesting Officer*      Commissioner of Patents and Trademarks

UNITED STATES PATENT AND TRADEMARK OFFICE
CERTIFICATE OF CORRECTION

PATENT NO. : 5,496,370
DATED : March 5, 1996
INVENTOR(S) : Robert S. Hamas

It is certified that error appears in the above-indentified patent and that said Letters Patent is hereby corrected as shown below:

Replace claim 13 with the following:
--13. A surgically implantable prosthetic device comprising:
    a sealable outer envelope defining an envelope interior and adapted to be filled with a fluid filler to maintain said fluid filler within said sealable outer envelope;
    an inner envelope positioned within the interior of said sealable outer envelope and adapted to be filled with said fluid filler; and
    a baffle means for decreasing the displacement rate of said fluid filler positioned within the interior of said inner envelope and attached to said inner envelope, said baffle means filling at least a portion of said envelope interior, wherein said baffle means allows for movement of said fluid filler through said baffle means in any direction and said inner envelope encloses said baffle means.--

Replace claim 14 with the following:
--14. The prosthetic device of claim 13, wherein a space is provided in said envelope interior which is not filled with said baffle means.--

Replace claim 15 with the following:
--15. The prosthetic device of claim 14, wherein said space is positioned between said baffle means and said envelope wherein said space substantially surrounds said baffle means.--

UNITED STATES PATENT AND TRADEMARK OFFICE
CERTIFICATE OF CORRECTION

PATENT NO.  : 5,496,370
DATED       : March 5, 1996
INVENTOR(S) : Robert S. Hamas It is certified that error appears in the above-indentified patent and that said Letters Patent is hereby corrected as shown below:

Replace claim 16 with the following:
--16. The prosthetic device of claim 14, wherein a said baffle means is positioned at a plurality of locations within said envelope interior.--

Claim 17 Line 41 Column 6 delete "15" and insert --13--.

Replace claim 19 with the following:
--19. The prosthetic device of claim 13, wherein said inner envelope is porous adapted to allow said fluid filler to flow therethrough.--

Signed and Sealed this

Eleventh Day of March, 1997

Attest:

BRUCE LEHMAN

*Attesting Officer*     *Commissioner of Patents and Trademarks*